United States Patent
Yokomizo

(10) Patent No.: US 9,872,945 B2
(45) Date of Patent: Jan. 23, 2018

(54) BLOOD TREATMENT FILTER, BLOOD CIRCUIT, AND BLOOD TREATMENT METHOD

(71) Applicant: ASAHI KASEI MEDICAL CO., LTD., Tokyo (JP)

(72) Inventor: Tomohisa Yokomizo, Tokyo (JP)

(73) Assignee: ASAHI KASEI MEDICAL CO., LTD., Tokyo (JP)

( * ) Notice: Subject to any disclaimer, the term of this patent is extended or adjusted under 35 U.S.C. 154(b) by 0 days.

(21) Appl. No.: 14/416,458

(22) PCT Filed: Jul. 25, 2013

(86) PCT No.: PCT/JP2013/070229
§ 371 (c)(1),
(2) Date: Jan. 22, 2015

(87) PCT Pub. No.: WO2014/017604
PCT Pub. Date: Jan. 30, 2014

(65) Prior Publication Data
US 2015/0265756 A1    Sep. 24, 2015

(30) Foreign Application Priority Data
Jul. 25, 2012    (JP) .................. 2012-164851

(51) Int. Cl.
*A61M 1/02*    (2006.01)
*A61M 1/36*    (2006.01)
(Continued)

(52) U.S. Cl.
CPC ........ *A61M 1/0281* (2013.01); *A61M 1/0218* (2014.02); *A61M 1/3496* (2013.01);
(Continued)

(58) Field of Classification Search
CPC .............. A61M 1/3633; A61M 1/0236; A61M 1/0222; A61M 1/0231; A61M 1/0218;
(Continued)

(56) References Cited

U.S. PATENT DOCUMENTS

| 4,190,426 A | * | 2/1980 | Ruschke | ................. | A61M 5/36 |
| | | | | | 128/205.12 |
| 5,707,520 A | | 1/1998 | Kuroki et al. | | |

(Continued)

FOREIGN PATENT DOCUMENTS

| EP | 0620017 | 10/1994 |
| EP | 2554190 | 2/2013 |

(Continued)

OTHER PUBLICATIONS

Search report from E.P.O., dated Jul. 8, 2015.
(Continued)

*Primary Examiner* — Katherine Zalasky
*Assistant Examiner* — Benjamin L Lebron
(74) *Attorney, Agent, or Firm* — Greenblum & Bernstein, P.L.C.

(57) ABSTRACT

A blood treatment filter including: a filter container that introduces blood from an inlet into an internal space, and discharges treated blood from an outlet; a filter material that is housed in the filter container to partition the internal space into an inlet side space and an outlet side space, and filters the passing blood to remove a specific component; an inlet port that forms an inlet channel through which the blood flowing from the inlet to the internal space passes; an outlet port that forms an outlet channel through which the blood flowing from the internal space to the outlet passes, wherein the outlet channel has a tapered outlet passage with an inner diameter increasing from the internal space side toward the outlet side.

8 Claims, 11 Drawing Sheets

(51) Int. Cl.
  *B01D 69/06* (2006.01)
  *A61M 5/36* (2006.01)
  *A61M 1/34* (2006.01)

(52) U.S. Cl.
  CPC ........ *A61M 1/3633* (2013.01); *A61M 1/3635* (2014.02); *A61M 1/3636* (2014.02); *A61M 5/36* (2013.01); *B01D 69/06* (2013.01); *A61M 2202/0439* (2013.01)

(58) Field of Classification Search
  CPC .............. A61M 1/3636; A61M 1/3496; A61M 1/3635; A61M 1/0281; A61M 1/1658; A61M 2202/0439; A61M 5/36; B01D 69/06; B01D 69/10
  See application file for complete search history.

(56) References Cited

U.S. PATENT DOCUMENTS

| | | | |
|---|---|---|---|
| 5,798,041 A * | 8/1998 | Zuk, Jr. | A61M 1/3627 210/435 |
| 6,168,718 B1 | 1/2001 | Sutter et al. | |
| 6,231,770 B1 | 5/2001 | Bormann et al. | |
| 2005/0051486 A1 | 3/2005 | Zuk, Jr. | |
| 2009/0084719 A1 * | 4/2009 | Childers | A61M 1/1658 210/151 |
| 2009/0173685 A1 * | 7/2009 | Imai | A61M 1/3633 210/243 |

FOREIGN PATENT DOCUMENTS

| | | |
|---|---|---|
| GB | 2 043 478 | 10/1980 |
| JP | 55-116417 | 9/1980 |
| JP | 2001-500053 | 1/2001 |
| JP | 2010-518962 | 6/2010 |
| JP | 2011-212174 | 10/2011 |
| JP | 4934133 | 5/2012 |
| JP | 2012-139347 | 7/2012 |
| WO | 2008/103142 | 8/2008 |
| WO | 2011/125617 | 10/2011 |

OTHER PUBLICATIONS

Search report from International Patent Appl. No. PCT/JP2013/070229, dated Oct. 29, 2013.

English translation of Written Opinion of the International Searching Authority in PCT/JP2013/070229, dated Feb. 5, 2015.

* cited by examiner

Fig.7
(a)
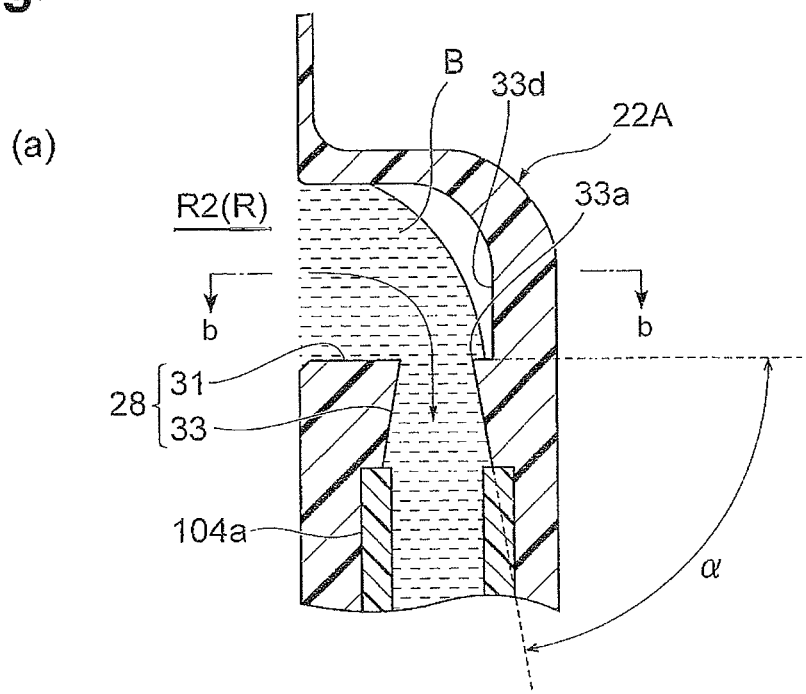
(b)
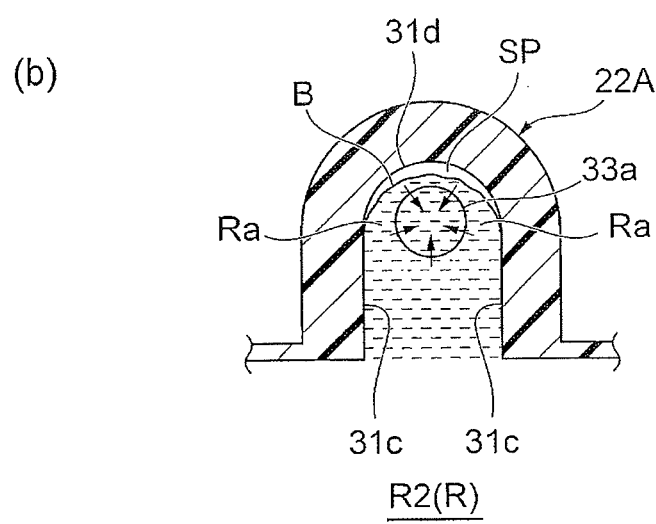

Fig.8
(a)
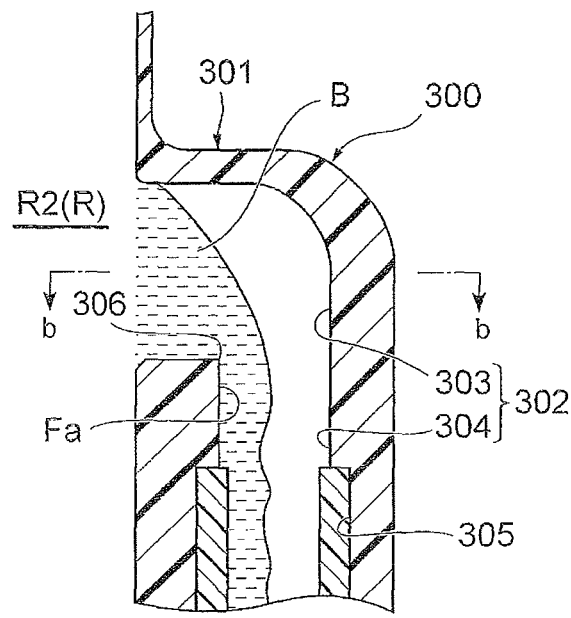
(b)
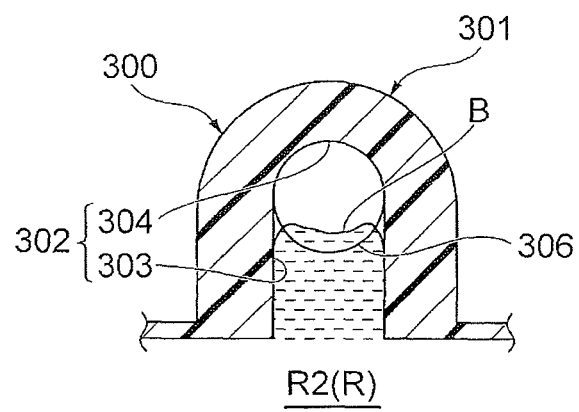

Fig.10
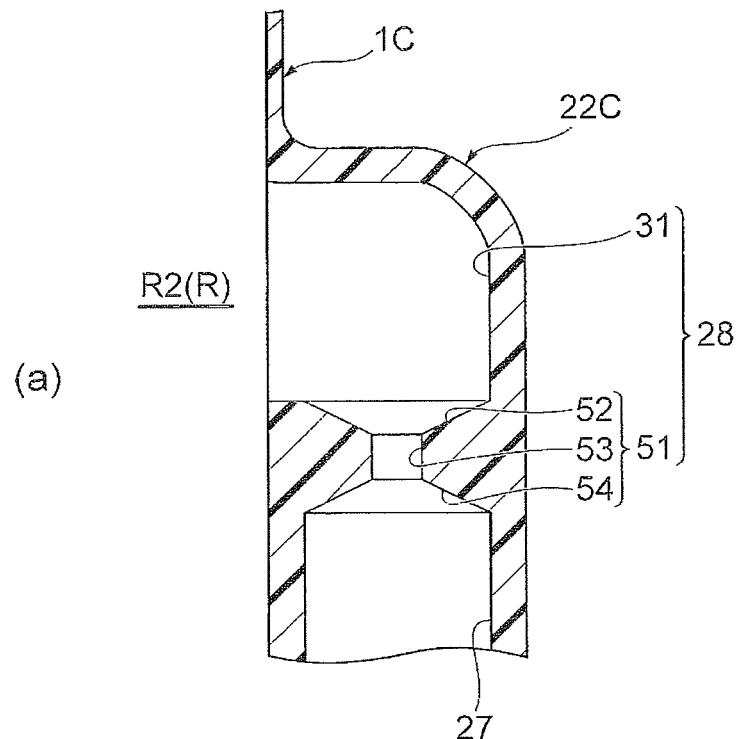
(a)
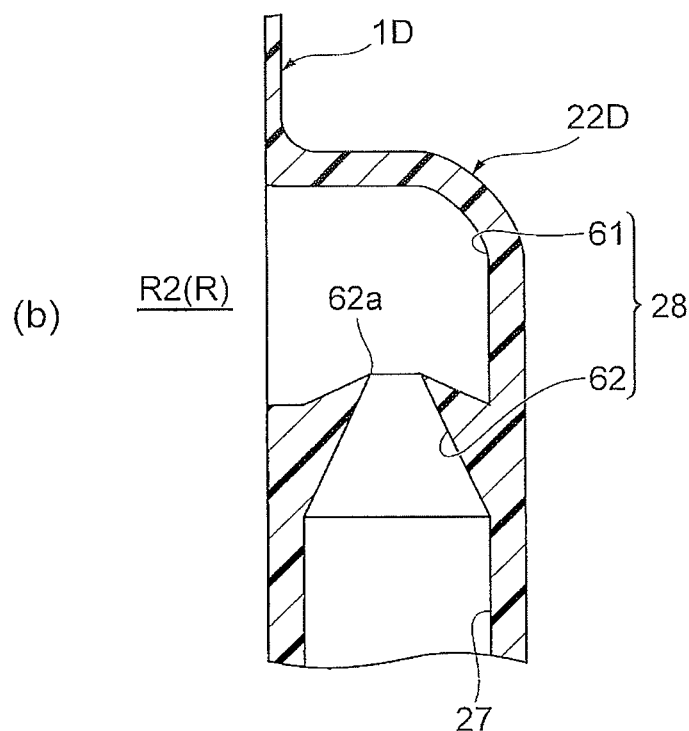
(b)

Fig.11
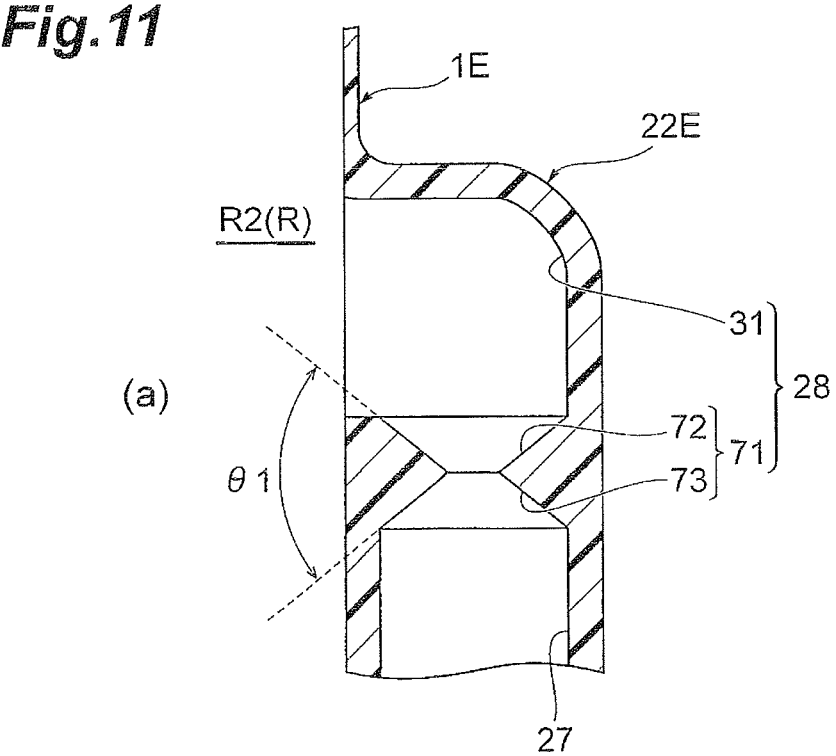
(a)
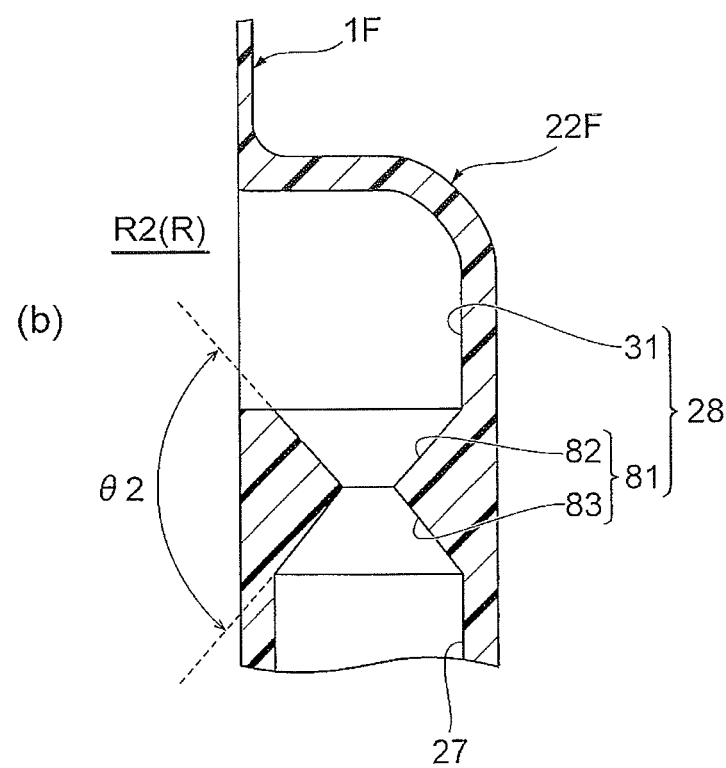
(b)

BLOOD TREATMENT FILTER, BLOOD CIRCUIT, AND BLOOD TREATMENT METHOD

TECHNICAL FIELD

The present invention relates to a blood treatment filter, a blood circuit including the blood treatment filter, and a blood treatment method using the blood treatment filter.

BACKGROUND ART

In the field of blood transfusion, so-called leukapheresis is in widespread use, which is removing mixed leukocytes contained in a blood preparation and then transfusing the blood preparation. This is because it has been clarified that relatively minor side effects such as headache, nausea, chill, or febrile non-hemolytic transfusion reaction associated with blood transfusion, or serious side effects such as alloantigen sensitization, viral infection, or GVHD after blood transfusion that seriously affect recipients are mainly caused by leukocytes mixed in a blood preparation used for blood transfusion. There are several methods for removing leukocytes, and among them, a filter method is currently in widespread use because it has advantages such as high leukocyte removal performance, a simple operation, and low cost. In the filter method, for example, a filter (blood treatment filter) as disclosed in Patent Literature 1 is used.

Treatment of a blood preparation or the like by using the blood treatment filter of this type has been often performed at the bedside in a blood transfusion operation, while in recent years, to ensure quality management of a blood preparation from which leukocytes are removed, filtration is generally performed in each blood center. Usually, in filtering blood by using a blood treatment filter in a blood center, it is general that a blood bag containing a blood preparation to be filtered is placed on a position 20 cm to 100 cm higher than the filter, and at the same time, a blood collection bag that collects filtered blood is placed on a position 30 cm to 120 cm lower than the filter, and the blood preparation is filtered by the effect of gravity.

CITATION LIST

Patent Literature

Patent Literature 1: National Publication of International Patent Application No. 2010-518962

SUMMARY OF INVENTION

Technical Problem

However, in performing filtration by using the effect of gravity from a height differential, it is sometimes difficult to obtain a desired filtration speed depending on states of a blood circuit through which the blood preparation or the like passes.

Thus, the present invention has an object to provide a blood treatment filter, a blood circuit, and a blood treatment method that obtain a desired filtration speed to allow efficient filtration treatment in performing filtration by using the effect of gravity from a height differential.

Solution to Problem

The present inventor has diligently studied causes of a reduction in filtration speed in performing filtration by using gravity from a height differential. Here, it has been found that if a liquid-tight state in a blood circuit is lost, the filtration speed is prone to decrease, and in a conventional blood treatment filter, particularly, a gas is prone to remain in an outlet port to lose a liquid-tight state. Then, the inventor has diligently studied measures for eliminating the loss of the liquid-tight state in this area, found that it is effective to form a tapered channel with an inner diameter increasing in a flow direction of blood in an outlet port, and conceived the present invention.

Specifically, the present invention is a blood treatment filter that treats blood introduced from an inlet and discharges the blood from an outlet, the blood treatment filter comprising: a filter container that introduces the blood from the inlet into an internal space, and discharges the treated blood from the outlet; a filter material that is housed in the filter container to partition the internal space into an inlet side space and an outlet side space, and filters the passing blood to remove a specific component; an inlet port that forms a blood introduction passage through which the blood flowing from the inlet to the internal space passes; and an outlet port that forms a blood lead-out passage through which the blood flowing from the internal space to the outlet passes, wherein the blood lead-out passage has an outlet tapered portion with an inner diameter increasing from the internal space side toward the outlet side. The blood includes blood preparations such as whole blood preparations, erythrocyte preparations, thrombocyte preparations and blood plasma preparations for blood transfusion.

Since the filter material has predetermined liquid passing resistance, a liquid flow rate per unit time is lower than a case of transferring blood without using the filter material. Thus, it is sometimes difficult for a conventional blood treatment filter to ensure a sufficient flow rate to push out all air existing in the outlet port, and in such a case, air sometimes remains in the outlet port. In this case, a flow of blood along a wall surface of the outlet side circuit sometimes enters a kind of equilibrium state while being unable to push out all the air existing in the outlet port. Also, in introducing a liquid into a dry filter material, the liquid and a gas alternately flow into the outlet port within a certain time before the gas in the filter material is completely replaced by the liquid. Thus, even if the liquid-tight state is once formed, further entry of bubbles causes air to remain in the outlet port. As a result, the liquid-tight state is lost in the outlet port, and blood merely flows along the wall surface, and the filtration speed is prone to decrease. As described above, a length of a channel that is not in the liquid-tight state does not contribute to provide a flow force by using gravity from a height differential.

In contrast to this, the outlet tapered portion with an inner diameter increasing from the internal space side toward the outlet side is provided in the blood lead-out passage of the present invention, and according to the present inventor's findings, the outlet tapered portion provides a trigger for blood to push out bubbles during flowing, which can facilitate formation of a liquid-tight state, and prevent a reduction in filtration speed. Thus, a desired filtration speed is obtained to allow efficient filtration treatment.

Also, in the present invention, it is preferable that in a case of cutting the outlet port along an imaginary surface including a central axis in a channel direction of the outlet tapered portion, a section of a starting point portion on the internal space side of the outlet tapered portion is acute-angled. The starting point portion on the internal space side of the outlet tapered portion is an inlet through which blood enters the outlet tapered portion. The section of the starting point portion of the outlet tapered portion being acute-angled means that an angle of a portion in which blood flows in this inlet is a large angle exceeding 270 degrees. Specifically, when blood enters the outlet tapered portion from the inlet, the blood needs to flow along the wall surface and go around to a back side by an angle exceeding 270 degrees, and smooth entry along the wall surface is controlled. Thus, the blood flowing while maintaining a fixed contact angle with respect to a material that forms the outlet port is prone to flow along the wall surface in a circling direction of the starting point portion rather than go around to the back side in the starting point portion of the outlet tapered portion. Therefore, the blood trying to flow along the wall surface seems to be stuck before being introduced into the outlet tapered portion. As a result, the blood spreading in the circling direction in the starting point portion of the outlet tapered portion forms a wide flow, and a trigger to push out internally accumulating bubbles is created, which is more effective for forming a liquid-tight state.

Also, in terms of controlling smooth entry of blood in the outlet tapered portion, and preventing the blood from going around to a back side to flow along the wall surface, as described above, the angle of the portion in which blood flows is effectively an angle larger than 270 degrees, and more effectively an angle of 280 degrees or more. To achieve smooth traveling of blood, there is no problem in this angle being large, while in terms of easiness in shaping, maintenance of a shape, or strength of the outlet port, the angle of the portion in which blood flows is preferably 330 degrees or less, and more preferably 315 degrees or less.

Also, in the present invention, it is preferable that the blood lead-out passage comprises an outlet anterior chamber that communicates with the internal space, an outlet connection channel that communicates with the outlet and has the outlet tapered portion, and a draw-in opening that provides communication between the outlet anterior chamber and the outlet connection channel, the outlet anterior chamber has a lower surface, and the draw-in opening is provided in a part of the lower surface of the outlet anterior chamber. With this configuration, when the blood enters the outlet tapered portion from the draw-in opening, the blood can flow along the lower surface of the outlet anterior chamber, the blood spreading in the circling direction of the draw-in opening forms a wide flow, and a trigger to push out internally accumulating bubbles is created, which is more effective for forming a liquid-tight state.

It is preferable that the outlet anterior chamber further comprises a pair of side surfaces facing each other with the draw-in opening therebetween, and an inner diameter of the draw-in opening is smaller than a separation distance between the pair of side surfaces. In this configuration, a channel that serves as a side path for the blood is formed between the draw-in opening and at least one side surface of the outlet anterior chamber. Thus, the blood does not locally enter the outlet tapered portion only from the front of the draw-in opening, but also enters from the side of the draw-in opening through the side path, and the blood widely spreads in the outlet anterior chamber, which is more effective for forming a liquid-tight state.

Also, it is preferable that the draw-in opening is provided closer to the internal space side than an outlet deepest portion most distant from the internal space in the outlet anterior chamber. Since a space is also formed on a deep side of the draw-in opening, the blood passes beside the draw-in opening, goes around to the deep side, and enters the outlet tapered portion from a broader range. Thus, the blood widely spreads in the outlet anterior chamber, which is more effective for forming a liquid-tight state.

Further, in terms of ensuring a sufficient flow of blood and preventing a reduction in flow speed, a diameter of the draw-in opening is preferably 1 mm or more, and more preferably 1.5 mm or more. On the other hand, in terms that the blood efficiently spreads in the circling direction of the draw-in opening to form a wide flow to easily form a liquid-tight state, the diameter of the draw-in opening is preferably 4 mm or less and more preferably 3 mm or less.

Also, the blood introduction passage of the present invention preferably has an inlet tapered portion with an inner diameter decreasing from the inlet side toward the internal space side. In a case of passing an erythrocyte preservation solution through the blood treatment filter and mixing the erythrocyte preservation solution with packed erythrocytes while priming, the erythrocyte preservation solution is discharged from the inlet. Providing the inlet tapered portion in the blood introduction passage can facilitate formation of a liquid-tight state in the blood introduction passage, and prevent a reduction in filtration speed in priming. Thus, a desired filtration speed is obtained to allow efficient priming treatment. In particular, in a case of mixing an erythrocyte preservation solution with packed erythrocytes by priming and then reversing a blood circuit to perform filtration treatment of blood, if air remains in the inlet tapered portion, the air may flow into and blocks the filter material, but the above configuration can reduce the risk.

it is preferable that in a case of cutting the inlet port along an imaginary surface including a central axis in a channel direction of the inlet tapered portion, a section of an end point portion on the internal space side of the inlet tapered portion is acute-angled. In this configuration, the same advantage as when the section of the starting point portion on the internal space side of the outlet tapered portion is acute-angled, a trigger to push out internally accumulating bubbles is created in priming treatment, which is more effective for forming a liquid-tight state.

It is preferable that the blood introduction passage described above comprises an inlet posterior chamber that communicates with the internal space, an inlet connection channel that communicates with the inlet and has the inlet tapered portion, and a communication opening that provides communication between the inlet posterior chamber and the inlet connection channel, the inlet posterior chamber has an upper surface, and the communication opening is provided in a part of the upper surface of the inlet posterior chamber. With this configuration, a trigger to push out internally accumulating bubbles is created, which is more effective for forming a liquid-tight state.

Also, it is preferable that the inlet posterior chamber further comprises a pair of side surfaces facing each other with the communication opening therebetween, and an inner diameter of the communication opening is smaller than a separation distance between the pair of side surfaces. In this configuration, the blood widely spreads in the inlet posterior chamber in priming treatment, which is more effective for forming a liquid-tight state.

Also, it is preferable that the communication opening is provided closer to the internal space side than an inlet deepest portion most distant from the internal space in the inlet posterior chamber. In this configuration, the blood widely spreads in the inlet posterior chamber, which is more effective for forming a liquid-tight state.

Also, a blood circuit according to the present invention comprises: the blood treatment filter described above; a storage bag that stores blood; a collection bag that stores blood after treatment with the blood treatment filter; an inlet side circuit portion that connects the storage bag and the inlet port of the blood treatment filter; and an outlet side circuit portion that connects the outlet port of the blood treatment filter and the collection bag. According to this blood treatment system, a desired filtration speed is obtained to allow efficient filtration treatment.

Also, a blood treatment method according to the present invention uses the blood treatment filter described above and filters blood by using gravity from a height differential. According to this blood treatment method, a desired filtration speed is obtained to allow efficient filtration treatment.

Advantageous Effects of Invention

According to the present invention, in a case of performing filtration by using gravity from a height differential, a desired filtration speed is obtained to allow efficient filtration treatment.

BRIEF DESCRIPTION OF DRAWINGS

FIG. 7 shows a flow of blood in an outlet port, (a) is a vertical sectional view of the outlet port, and (b) is a sectional view taken along the line b-b in (a).

FIG. 8 shows a flow of blood in an outlet port according to a reference form, (a) is a vertical sectional view of the outlet port, and (b) is a sectional view taken along the line b-b in (a).

FIG. 10 shows, in an enlarged manner, outlet ports of blood treatment filters according to other embodiments of the present invention, (a) is a sectional view showing, in an enlarged manner, an outlet port of a blood treatment filter according to a third embodiment, and (b) is a sectional view showing, in an enlarged manner, an outlet port of a blood treatment filter according to a fourth embodiment.

FIG. 11 shows, in an enlarged manner, outlet ports of blood treatment filters according to other embodiments of the present invention, (a) is a sectional view showing, in an enlarged manner, an outlet port of a blood treatment filter according to a fifth embodiment, and (b) is a sectional view showing, in an enlarged manner, an outlet port of a blood treatment filter according to a sixth embodiment.

DESCRIPTION OF EMBODIMENTS

Now, with reference to the drawings, preferred embodiments of a blood treatment filter according to the present invention will be described in detail. The blood treatment filter is a filter for removing undesirable components (specific component) such as aggregates or leukocytes, etc., from blood. The blood described in the embodiments includes blood preparations such as whole blood preparations, erythrocyte preparations, thrombocyte preparations, and blood plasma preparations for blood transfusion.

An outline of the blood treatment filter may adopt various shapes such as a rectangular shape, a disk shape, an elliptic shape, or an oval shape, but the rectangular shape is preferable to reduce material loss in manufacturing. Thus, the embodiments below are described for the rectangular shape as an example.

First Embodiment

Figure 1:
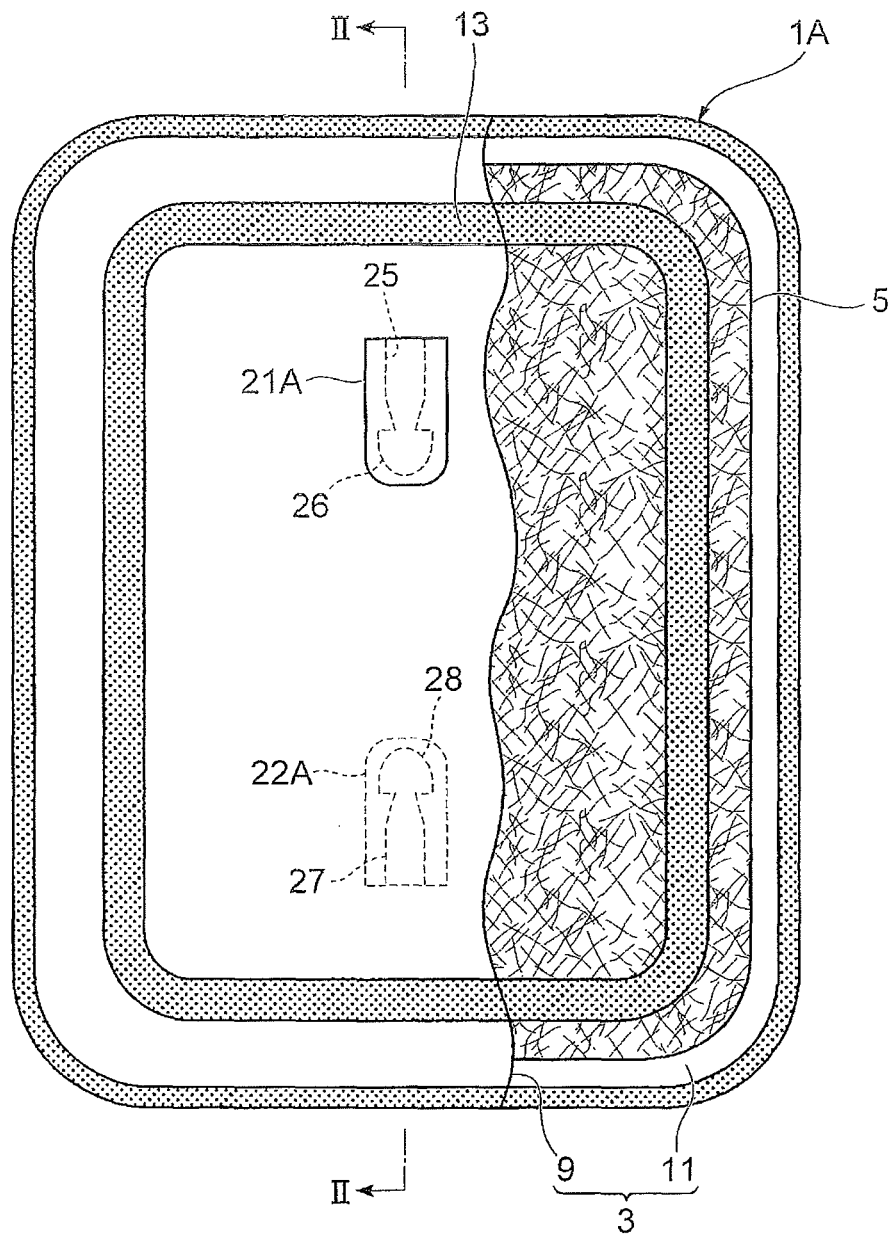
FIG. 1 is a partially cutaway plan view showing a blood treatment filter according to a first embodiment of the present invention.

First, with reference to FIG. 1 and FIG. 2, a blood treatment filter 1A according to a first embodiment will be described. The blood treatment filter 1A comprises a flexible container (filter container) 3 having an inlet port 21A and an outlet port 22A for blood, and a sheet-like leukocyte removal filter material 5 (hereinafter referred to as "filter material 5") housed to partition an inside of the flexible container 3 into the inlet port 21A side and the outlet port 22A side.

The flexible container 3 is a container of a rectangular flat shape. The flat shape means a thin shape with a wide surface. The flexible container 3 includes a rectangular sheet-like inlet side container 9, and a rectangular sheet-like outlet side container 11. The inlet port 21A is sealed to the inlet side container 9. Sealing means securing by thermocompression bonding or adhesion or the like so that leak of a liquid can be prevented.

The inlet side container 9 and the outlet side container 11 overlap each other so as to sandwich the rectangular filter material 5. The inlet side container 9 and the outlet side container 11 are sealed along a peripheral edge of the filter material 5 while sandwiching the filter material 5. A strip-like adhesion region along the peripheral edge of the filter material 5 is a seal portion 13. The seal portion 13 rectangular annularly surrounds the inlet port 21A, and an internal space R inside the seal portion 13 is a filtration portion in which blood flows. Further, outer edges of the inlet side container 9 and the outlet side container 11 are sealed to annularly surround the seal portion 13.

The inlet port 21A sealed to the inlet side container 9 can be appropriately placed in an inside region surrounded by the seal portion 13. The inlet port 21A according to this embodiment is placed on one end side in a longitudinal direction of the flexible container 3, that is, on an upper side with the blood treatment filter 1A standing for blood treatment. In the inlet port 21A, an inlet channel (blood introduction passage) 26 is formed that receives untreated blood in forming an inlet side circuit 102 (see FIG. 6) in which blood flows. The inlet channel 26 communicates with the internal space R.

The outlet port 22A sealed to the outlet side container 11 can be appropriately placed in the inside region surrounded by the seal portion 13. The outlet port 22A according to this embodiment is placed on the other end side in the longitudinal direction of the flexible container 3, that is, on a lower side with the blood treatment filter 1A standing for blood treatment. In the outlet port 22A, an outlet channel (blood lead-out passage) 28 that discharges blood treated by the filter material 5 is formed in forming an outlet side circuit 104 (see FIG. 6) in which blood flows. The outlet channel 28 communicates with the internal space R.

The internal space R is partitioned by the filter material 5 into an inlet side space R1 and an outlet side space R2. The blood introduced from the inlet 25 is introduced through the inlet channel 26 to the inlet side space R1, passes through the filter material 5 and moves to the outlet side space R2, and is discharged through the outlet channel 28 from the outlet 27. When the blood passes through the filter material 5, leukocytes in the blood are filtered and removed, and thus blood from which leukocyte components are almost removed is obtained from the outlet 27.

Next, aspects of materials or shapes of components that constitute the blood treatment filter 1A will be described.

As described above, the flexible container 3 is formed of the inlet side container 9 and the outlet side container 11. As flexible resin used for the flexible container 3, soft polyvinyl chloride, polyolefin, or thermoplastic elastomer mainly containing the same are favorably used in terms of good permeability of high-pressure steam or electron beam for sterilization and further having toughness to withstand load in centrifuging.

Examples of the filter material 5 include a fiber structure such as nonwoven fabric manufactured by a melt blowing method or the like, a porous material having continuous pores (sponge-like structure), or a leukocyte removal filter material formed of a porous film or the like. In a case where a base material that forms the leukocyte removal filter material is a fiber structure, examples of the material include polyester, polypropylene, polyamide, polyacrylonitrile, polytrifluoroethylene, polymethyl methacrylate, polystyrene, or the like. Further, in the case where the fiber structure is used as the base material, the base material may be a base material formed of fibers having substantially uniform fiber diameters, or a base material in which a plurality of types of fibers having different fiber diameters are mixed as disclosed in WO 97/232266. To reduce the number of leukocytes mixed in blood to $5 \times 10^6$/unit or less after filtration, an average fiber diameter of base material fibers that form the leukocyte removal filter material is preferably 3.0 µm or less, and more desirably 0.9 to 2.5 µm.

In a case where the base material that forms the leukocyte removal filter material is a porous material or a porous film, examples of the material include any materials such as polyacrylonitrile, polysulfone, cellulose acetate, polyvinyl formal, polyester, polyacrylate, polymethacrylate, or polyurethane. To reduce the number of leukocytes mixed in blood to $5 \times 10^6$/unit or less after filtration, an average hole diameter of the porous material or the porous film is desirably 2 µm or more and less than 10 µm.

Also, the leukocyte removal filter material may be formed of the base material itself, or by chemically or physically reforming a surface thereof, and any leukocyte removal filter materials are included in the sheet-like filter material 5 that contributes to leukocyte removal. The leukocyte removal filter material may use the fiber structure, the porous material, or the porous film in a single layer or in a combination of a plurality of layers.

Examples of a method for cutting the leukocyte removal filter material include cutting with an edge, cutting with an ultrasonic cutter, cutting with a laser, or the like.

The inlet port 21A and the outlet port 22A are members that are less prone to be deformed than conduits 102a, 104a described later.

"Members that are less prone to be deformed" refer to members with a small deformation amount by an external force, and include, for example, a case where the inlet port 21A and the outlet port 22A are formed of a harder material than that for the conduits 102a, 104a (see FIG. 6) to reduce the deformation amount. "Formed of a harder material" includes a case where even if the material for the inlet port 21A and the outlet port 22A is, for example, what is called "vinyl chloride" like the material for the conduits 102a, 104a, a physical property differs depending on differences in molecular weights or amounts of contained plasticizer, and the material shows a harder physical property than the material for the conduits 102a, 104a. Also, "external force" described above includes, for example, an external force generated by a pressure difference between pressure in a hollow portion and atmospheric pressure.

Also, "members that are less prone to be deformed" include, for example, a case where even if the inlet port 21A and the outlet port 22A are of the same material as the conduits 102a, 104a, the inlet port 21A and the outlet port 22A are thicker than the conduits 102a, 104a to reduce the deformation amount.

In this embodiment, the inlet port 21A and the outlet port 22A are soft resin moldings, and as the material for the inlet port 21A and the outlet port 22A, for example, vinyl chloride or the like is favorably used. Even if the inlet port 21A and the outlet port 22A are of the same material as the conduits 102a, 104a to be connected, the inlet port 21A and the outlet port 22A are resin moldings and may have a thickness above a certain level, and thus may be harder than the conduits 102a, 104a and less prone to be deformed by the external force.

Figure 2:
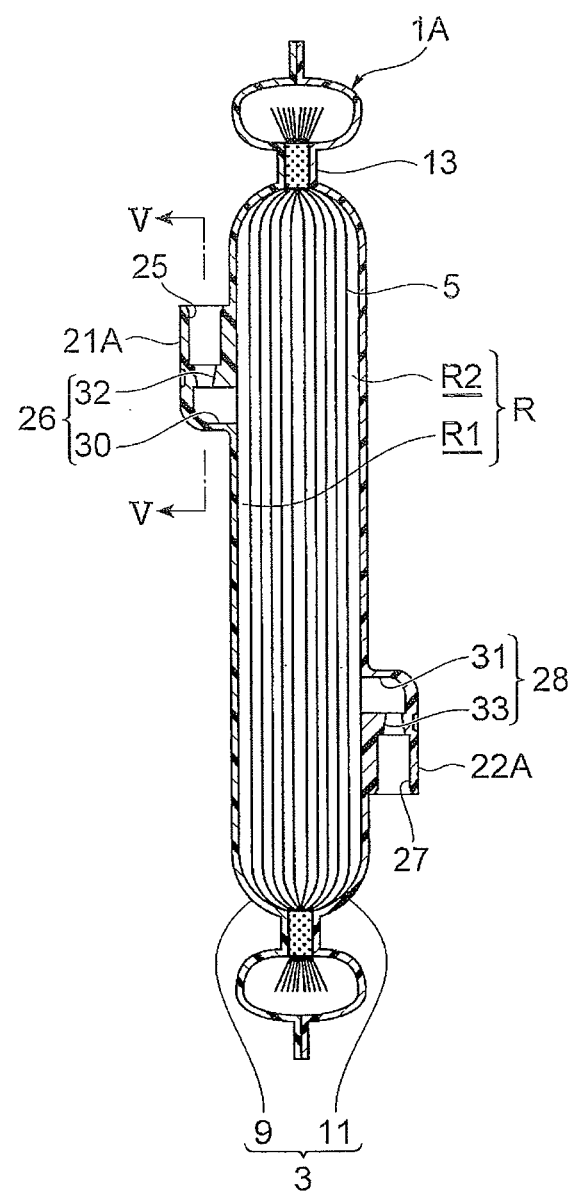
FIG. 2 is a sectional view taken along the line II-II in FIG. 1.

As shown in FIG. 2, the inlet port 21A protrudes from the inlet side container 9, and the outlet port 22A protrudes from the outlet side container 11. The inlet port 21A and the outlet port 22A according to this embodiment are point-symmetric with respect to a center of the filter material 5, and have substantially the same configuration. Specifically, a port on an upstream side is the inlet port 21A and a port on a downstream side is outlet port 22A in filtering blood in actual use.

Figure 3:
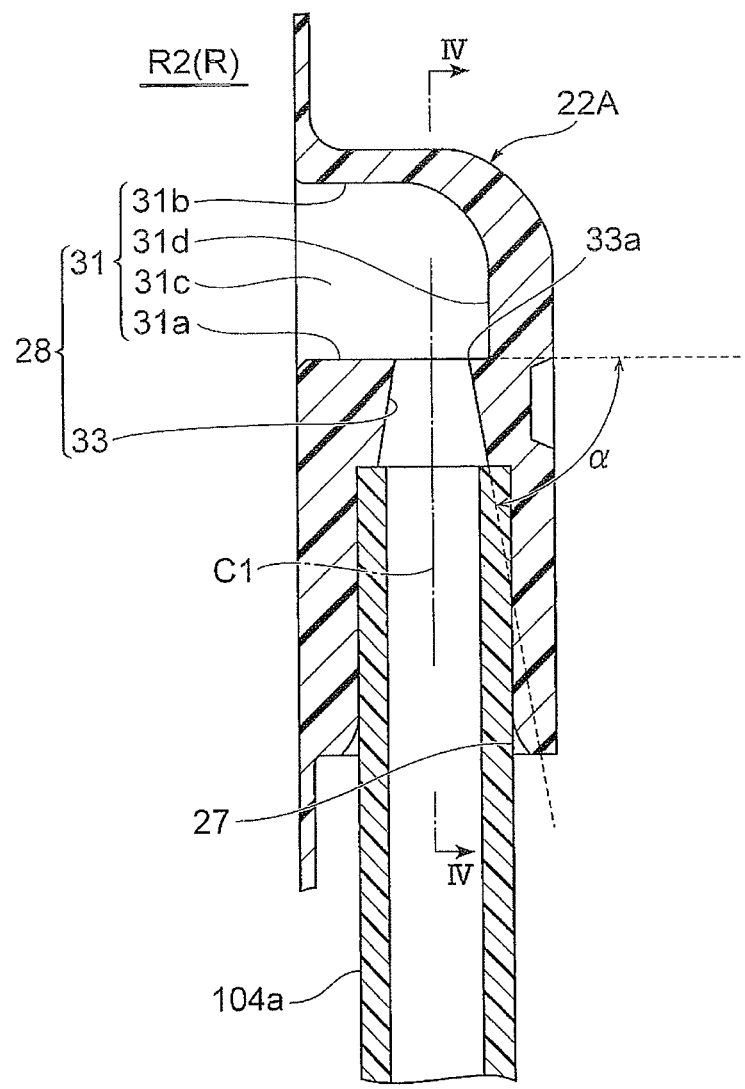
FIG. 3 is a sectional view showing an outlet port in an enlarged manner.
Figure 4:
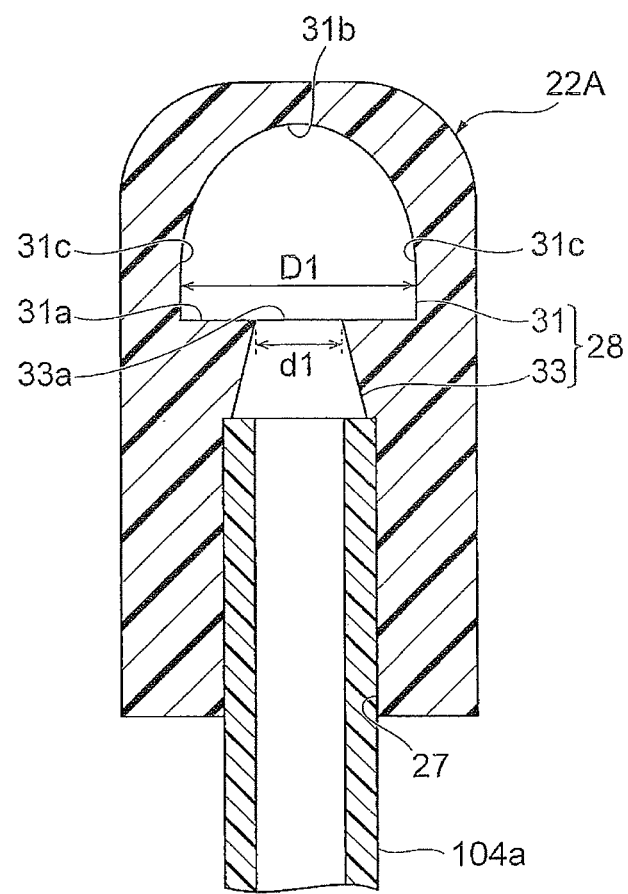
FIG. 4 is a sectional view taken along the line IV-IV in FIG. 3.

As shown in FIG. 3 and FIG. 4, in the outlet port 22A, an outlet channel 28, and an outlet 27 into which the conduit 104a is inserted to be fitted are formed. In the outlet channel 28, a chamber (outlet anterior chamber) 31 that communicates with the outlet side space R2, and a tapered outlet passage (outlet tapered portion) 33 that communicates with the chamber 31 are provided, and the outlet 27 connects to a downstream end of the tapered outlet passage 33. In this embodiment, the tapered outlet passage 33 corresponds to an outlet connection channel.

The chamber 31 has a vertically long floor surface (lower surface) 31a, a dome-shaped ceiling surface 31b, a pair of left and right side surfaces 31c rising from opposite sides of the floor surface 31a and connecting to the ceiling surface 31b, and an end surface (outlet deepest portion) 31d on a deep side of the floor surface 31a. In the floor surface 31a, a draw-in opening 33a that communicates with the tapered outlet passage 33 is provided. The pair of left and right side surfaces 31c face each other with the draw-in opening 33a therebetween, and an inner diameter d1 (see FIG. 4) of the draw-in opening 33a is smaller than a separation distance D1 between the pair of side surfaces 31c. An edge on the deep side of the draw-in opening 33a (see FIG. 3) is provided slightly forward (closer to the internal space R side) of the end surface 31d of the chamber 31.

The tapered outlet passage 33 is provided in a connection area with the chamber 31, and an inner diameter increases from the chamber 31 side on the internal space R side toward the outlet 27 side. Specifically, the tapered outlet passage 33 is shaped so that the diameter gradually increases in a flow direction of blood.

FIG. 3 is a sectional view when cutting the outlet port 22A along an imaginary surface including a central axis C1 in a channel direction of the tapered outlet passage 33. As shown in FIG. 3, in this embodiment, an angle α of a section of a starting point portion of the tapered outlet passage 33, that is, an area in which the draw-in opening 33a is formed is acute.

Figure 5:
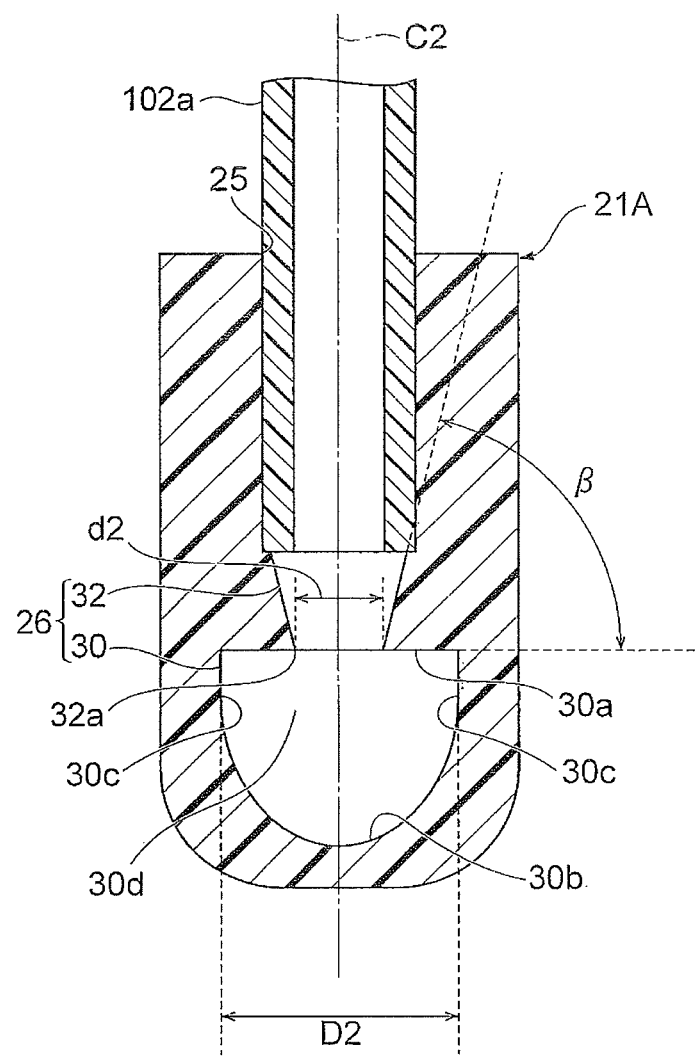
FIG. 5 is a sectional view showing an inlet port, taken along the line V-V in FIG. 2.

As shown in FIG. 2 and FIG. 5, in the inlet port 21A, an inlet channel 26, and an inlet 25 into which the conduit 102a is inserted to be fitted are formed. In the inlet channel 26, a chamber (inlet posterior chamber) 30 that communicates with the inlet side space R1, and a tapered inlet passage (inlet tapered portion) 32 that communicates with the chamber 30 are provided, and the inlet 25 connects to an upstream end of the tapered inlet passage 32. In this embodiment, the tapered inlet passage 32 corresponds to an inlet connection channel.

The chamber 30 has a vertically long ceiling surface (upper surface) 30a, a dome-shaped floor surface 30b, a pair of left and right side surfaces 30c rising from opposite sides of the floor surface 30b and connecting to the ceiling surface 30a, and an end surface 30d (inlet deepest portion) on a deep side of the ceiling surface 30a. In the ceiling surface (upper surface) 30a, a communication opening 32a that communicates with the tapered inlet passage 32 is provided. The pair of left and right side surfaces 30c face each other with the communication opening 32a therebetween, and an inner diameter d2 of the communication opening 32a is smaller than a separation distance D2 between the pair of side surfaces 31c. An edge on the deep side of the communication opening 32a is provided slightly closer to the internal space R side than the end surface 30d of the chamber.

The tapered inlet passage 32 is provided in a connection area to the chamber 30, and an inner diameter decreases from the inlet 25 side toward the chamber 30 side on the internal space R side. Specifically, the tapered inlet passage 32 is shaped so that the diameter gradually decreases in the flow direction of blood.

FIG. 5 is a sectional view when cutting the inlet port 21A along an imaginary surface including a central axis C2 in a channel direction of the tapered inlet passage 32. As shown in FIG. 5, in this embodiment, an angle β of a section of an end point portion of the tapered inlet passage 32, that is, an area in which the communication opening 32a is formed is acute.

Figure 6:
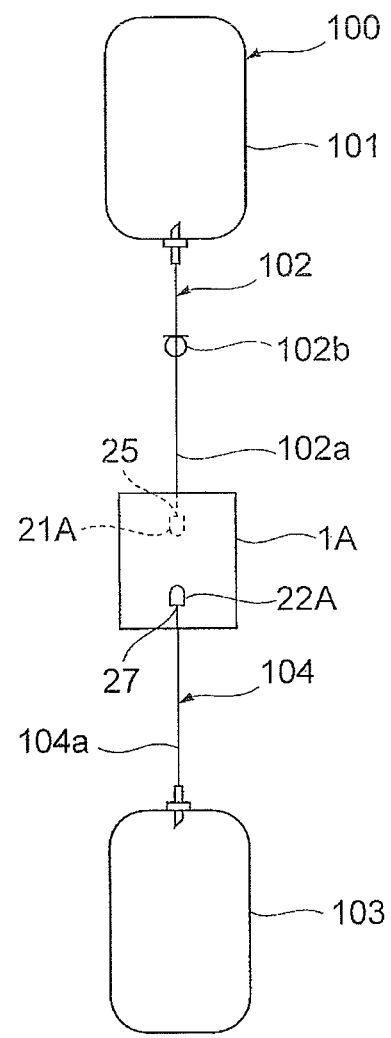
FIG. 6 is a schematic plan view showing a blood circuit.

Next, a blood circuit 100 comprising the blood treatment filter 1A according to the first embodiment, and a use state of the blood treatment filter 1A will be described with reference to FIG. 6. FIG. 6 is a front view showing an outline of the blood circuit 100.

The blood treatment filter 1A can be used for filtration by using gravity from a height differential. For example, the blood circuit 100 to which the blood treatment filter 1A is applied comprises a storage bag 101 containing collected blood, the blood treatment filter 1A, and a collection bag 103 that stores filtered blood. The storage bag 101 and the inlet port 21A of the blood treatment filter 1A are connected to each other by the conduit 102a such as a blood tube, and the collection bag 103 and the outlet port 22A of the blood treatment filter 1A are connected to each other by the conduit 104a such as a blood tube.

Further, to the conduit 102a on the upstream side, opening/closing means 102b or the like such as a roller clamp that opens/closes a channel is mounted, and an inlet side circuit 102 is formed of the conduit 102a, the opening/closing means 102b, or the like. An outlet side circuit 104 is formed of the conduit 104a or the like on the downstream side.

The conduit 102a is inserted into the inlet 25 of the blood treatment filter 1A, and the conduit 104a is inserted into the outlet 27 of the blood treatment filter 1A. Since the conduits 102a, 104a preferably have flexibility, tubes made of vinyl chloride or the like are preferably used as the conduits 102a, 104a.

Then, the storage bag 101 containing collected blood is placed in a position a predetermined distance, for example, about 50 cm higher than the blood treatment filter 1A, and the collection bag 103 that stores filtered blood is placed in a position a predetermined distance, for example, about 100 cm lower than the blood treatment filter 1A. Opening the channel of the blood circuit 100 causes filtration treatment of blood. Hereinafter, a difference in height between the storage bag 101 and the collection bag 103 is referred to as "filtration height".

Generally, in a case of performing blood filtration treatment using a blood treatment filter, the filter material has predetermined liquid passing resistance, and thus a liquid flow rate per unit time is smaller than a case of transferring blood without using the filter material. Thus, it is sometimes difficult for a conventional blood treatment filter to ensure a sufficient flow rate to push out all air existing in the outlet port, and in such a case, air sometimes remains in the outlet port to lose a liquid-tight state. In this case, a flow of blood along a wall surface of the outlet side circuit sometimes enters a kind of equilibrium state while being unable to push out all the air existing in the outlet port.

Also, in introducing a liquid into a dry filter material, the liquid and a gas alternately flow into the outlet port within a certain time before the gas in the filter material is completely replaced by the liquid. Thus, even if the liquid-tight state is once formed, further entry of bubbles causes air to remain in the outlet port, and the liquid-tight state is sometimes lost.

When the liquid-tight state is lost, for example, as shown in FIGS. 8(a) and 8(b), blood B merely flows along a wall surface Fa. Then, a principle of a siphon based on the liquid-tight state does not function, making it not possible to use the effect of gravity from a set height differential, and instead only enabling the actual use of gravity from a height differential reduced to a level at which the blood B is continuously present, thereby increasing a filtration time. As described above, a length of a channel that is not in the liquid-tight state does not contribute to providing a flow force caused by from gravity from a height differential.

FIG. 8 is a sectional view of an outlet port 301 of a blood treatment filter 300 according to a reference form. As shown in FIG. 8, in a case of the blood treatment filter 300, an outlet channel 302 has a chamber 303 and a communication channel 304, and the communication channel 304 connects the chamber 303 to the outlet 305. However, the communication channel 304 has a constant inner diameter in the flow direction of the blood B, and is not tapered. Also, an inner diameter of a draw-in opening 306 that is a starting point portion of the communication channel 304 is substantially the same as a separation distance between side surfaces of the chamber 303. Further, an edge on a deep side of the draw-in opening 306 is substantially continuous with an end surface of the chamber 303.

In the conventional blood treatment filter, in a case of a method of introducing an erythrocyte preservation solution from an outlet port side, passing the erythrocyte preservation solution through the filter material, and mixing the erythrocyte preservation solution with packed erythrocytes while priming, then, air sometimes remains in an inlet port. In this case, in reversing a blood circuit for filtration after mixing of the erythrocyte preservation solution with the packed erythrocytes, the air remaining in the blood circuit may flow into and block the filter material.

Occurrence frequency of the above described phenomenon differs depending on combinations of a set difference, resistance of the filter material, and viscosity of a liquid or the like. However, once this phenomenon occurs, differing from a set height differential for using gravity or an intended filtration speed causes problems in operability or performance.

The cause of loss of a liquid-tight state is that an air layer remains in the blood circuit 100 and is in an equilibrium state with blood flowing. Thus, breaking the equilibrium state can again form the liquid-tight state. Thus, for example, providing a trigger such as flipping the outlet port or once pinching and blocking the channel to eliminate the equilibrium state allows relatively easy release. However, it is difficult to perform this in the blood center or the like that treats a large amount of blood, and if blood flowing with remaining air covers an entire wall surface in the channel, there is a possibility of missing occurrence of a non-liquid-tight state.

For the above described problems, in the blood treatment filter 1A according to this embodiment, as shown in FIGS. 7(a) and 7(b), the tapered outlet passage 33 is provided in the outlet channel 28, and the inner diameter of the tapered outlet passage 33 is provided to increase from the internal space R side toward the outlet 27 side. The tapered outlet passage 33 provides a trigger for the blood B to push out bubbles during flowing, which can facilitate formation of the liquid-tight state, and prevent a reduction in filtration speed. Thus, a desired filtration speed is obtained to allow efficient filtration treatment.

Also, in the blood treatment filter 1A according to this embodiment, an angle cc of a section of a starting point portion of the tapered outlet passage 33 is acute. The starting point portion is an inlet from which the blood B enters the tapered outlet passage 33. The angle $\alpha$ of the section of the starting point portion of the tapered outlet passage 33 being acute means that an angle $(360°-\alpha)$ of a portion in which the blood B flows in the inlet is a large angle exceeding 270°.

Specifically, when the blood B enters the tapered outlet passage 33 from the inlet, the blood B needs to flow along the wall surface and go around to a back side by an angle exceeding 270 degrees, and smooth entry along the wall surface is controlled. Thus, the blood B flowing while maintaining a fixed contact angle with respect to a material that forms the tapered outlet passage 33 is prone to flow along the wall surface in a circling direction of the starting point portion rather than go around to the back side in the starting point portion of the tapered outlet passage 33. Therefore, the blood B trying to flow along the wall surface seems to be stuck before being introduced into the tapered outlet passage 33. As a result, the blood spreading in the circling direction forms a wide flow in the starting point portion of the tapered outlet passage 33, and a trigger to push out internally accumulating bubbles is created, which is more effective for forming a liquid-tight state.

Also, in terms of controlling smooth entry of the blood B in the tapered outlet passage 33, and preventing the blood B from going around to a back side to flow along the wall surface, as described above, the angle $(360°-\alpha)$ of the portion in which the blood B flows is effectively an angle larger than 270 degrees, and more effectively an angle of 280 degrees or more. To achieve smooth traveling of the blood B, there is no problem in this angle being large, while in terms of easiness in shaping, maintenance of a shape, or strength of the outlet port 22A, the angle of the portion in which the blood B flows is preferably 330 degrees or less, and more preferably 315 degrees or less.

Also, in the blood treatment filter 1A according to this embodiment, the draw-in opening 33a is provided in a part of the floor surface 31a of the chamber 31. Thus, when the blood B enters the tapered outlet passage 33 from the draw-in opening 33a, the blood B can flow along the floor surface 31a of the chamber 31, the blood B spreading in the circling direction of the draw-in opening 33a forms a wide flow, and a trigger to push out internally accumulating bubbles is created, which is more effective for forming a liquid-tight state.

Also, in the blood treatment filter 1A according to this embodiment, an inner diameter d1 of the draw-in opening 33a is smaller than a separation distance between the pair of side surfaces 31c facing each other with the draw-in opening 33a therebetween. Specifically, in this embodiment, a channel that serves as a side path Ra for the blood B is formed between the draw-in opening 33a and the side surface 31c of the chamber 31. Thus, the blood B does not locally enter the tapered outlet passage 33 only from the front of the draw-in opening 33a, but also enters from the side of the draw-in opening 33a through the side path Ra, and the blood widely spreads in the chamber 31, which is more effective for forming a liquid-tight state.

Also, the draw-in opening 33a is provided closer to the internal space R side than the end surface 31d (outlet deepest portion) most distant from the internal space R in the chamber 31. Specifically, since a space Sp is also formed on a deep side of the draw-in opening 33a, the blood B passes beside the draw-in opening 33a, goes around to the deep side, and enters the tapered outlet passage 33 from a broader range. Thus, the blood B widely spreads in the chamber 31, which is more effective for forming a liquid-tight state.

Further, in terms of ensuring a sufficient flow of the blood B and preventing a reduction in flow speed, the inner diameter d1 (diameter) of the draw-in opening 33a is preferably 1 mm or more, and more preferably 1.5 mm or more. On the other hand, in terms that the blood B efficiently spreads in the circling direction of the draw-in opening 33a to form a wide flow to easily form a liquid-tight state, the inner diameter d1 of the draw-in opening 33a is preferably 4 mm or less and more preferably 3 mm or less.

As shown in FIG. 2 and FIG. 5, in the blood treatment filter 1A, the tapered inlet passage 32 provided so that the inner diameter d1 decreases from the inlet 25 side toward the internal space R side is provided in the inlet channel 26. According to the blood treatment filter 1A, even in a case of a method of introducing an erythrocyte preservation solution from the outlet port 22A side of the blood treatment filter 1A, passing the erythrocyte preservation solution through the filter material 5, and mixing the erythrocyte preservation solution with packed erythrocytes while priming, the tapered inlet passage 32 provides a trigger for the erythrocyte preservation solution to push out bubbles during flowing, which can facilitate formation of a liquid-tight state, and prevent bubbles from remaining in the blood circuit 100.

In the blood treatment filter 1A, a section $\beta$ of an end point portion of the tapered inlet passage 32 is acute-angled. Thus, the same advantage is obtained as when the section $\alpha$ of the starting point portion on the internal space R side of the tapered outlet passage 33 is acute-angled, and a trigger to push out internally accumulating bubbles is created in priming treatment, which is more effective for forming a liquid-tight state. The angle $(360°-\beta)$ of the portion in which the blood B flows in the inlet port 21A is effectively an angle larger than 270 degrees, and more effectively an angle of 280 degrees or more. On the other hand, in terms of easiness in shaping, maintenance of a shape, or strength of the inlet port 21A, the angle of the portion in which the blood B flows is preferably 330 degrees or less, and more preferably 315 degrees or less.

In the blood treatment filter 1A, the communication opening 32a is formed in a part of the ceiling surface 30a of the chamber 30. Thus, a trigger to push out internally accumulating bubbles is created, which is more effective for forming a liquid-tight state.

Also, in the inlet channel 26 of the blood treatment filter 1A, the inner diameter d2 of the communication opening 32a is smaller than a separation distance D2 between the pair of side surfaces 30c facing each other with the communication opening 32a therebetween. Specifically, a channel that serves as a side path for the erythrocyte preservation solution is formed between the communication opening 32a and the side surface 30c of the inlet posterior chamber. Thus, the erythrocyte preservation solution does not locally enter the tapered inlet passage 32 only from the front of the communication opening 32a, but also enters from the side of the communication opening 32a through the side path, and the blood widely spreads in the chamber 30, which is more effective for forming a liquid-tight state.

Also, the communication opening 32a is provided closer to the internal space R side than the end surface 30d (inlet deepest portion) most distant from the internal space R in the chamber 30. Specifically, since a space is also formed on a deep side of the communication opening 32a, the erythrocyte preservation solution passes beside the communication opening 32a, goes around to the deep side, and enters the tapered inlet passage 32 from a broader range. Thus, the erythrocyte preservation solution widely spreads in the chamber 30, which is more effective for forming a liquid-tight state. The inner diameter (diameter) d2 of the communication opening 32a is preferably 1 mm or more, and more preferably 1.5 mm or more. On the other hand, the inner diameter d2 is preferably 4 mm or less, and more preferably 3 mm or less.

Second Embodiment

Figure 9:
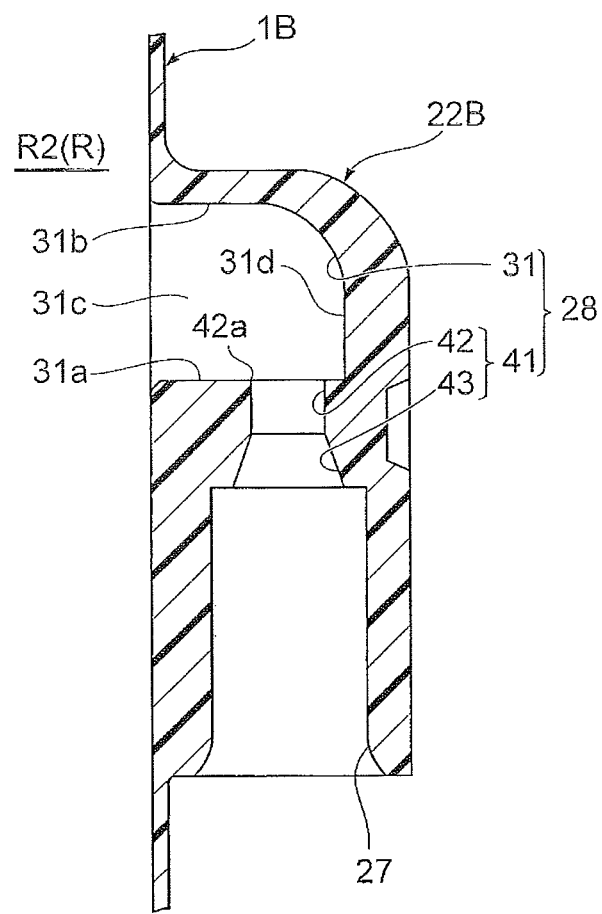
FIG. 9 is a sectional view showing, in an enlarged manner, an outlet port of a blood treatment filter according to a second embodiment of the present invention.

Next, with reference to FIG. 9, a blood treatment filter 1B according to a second embodiment will be described. In the blood treatment filter 1B, the same or similar components as in the blood treatment filter 1A are denoted by the same reference numerals, and overlapping descriptions will be omitted.

In an outlet port 22B of the blood treatment filter 1B according to this embodiment, an outlet channel (blood lead-out passage) 28, and an outlet 27 into which a conduit 104a is inserted to be fitted are formed. In the outlet channel 28, a chamber (outlet anterior chamber) 31 that communicates with an outlet side space R2, and an outlet connection channel 41 that communicates with the chamber 31 are provided. In the outlet connection channel 41, an intermediate channel 42 that communicates with the chamber 31, and a tapered outlet passage (outlet tapered portion) 43 are provided, and the outlet 27 connects to a downstream end of the tapered outlet passage 43.

An inner diameter of the intermediate channel 42 is constant in a flow direction of blood, and is formed of a cylindrical space. On the other hand, the tapered outlet passage 43 has an inner diameter increasing from the chamber 31 side on an internal space R side toward the outlet 27 side. Specifically, the tapered outlet passage 43 is shaped so that a diameter gradually increases in the flow direction of blood. An inner diameter of a draw-in opening 42a that is an inlet of the intermediate channel 42 is smaller than a separation distance between a pair of side surfaces 31c. An edge on the deep side the draw-in opening 42a is provided slightly forward (closer to the internal space R side) of an end surface 31d of the chamber 31.

According to this embodiment, the tapered outlet passage 43 provides a trigger for blood to push out bubbles during flowing, which can facilitate formation of a liquid-tight state, and prevent a reduction in filtration speed. Thus, a desired filtration speed is obtained to allow efficient filtration treatment.

Also, in the blood treatment filter 1B according to this embodiment, an inner diameter of the draw-in opening 42a is smaller than a separation distance between a pair of side surfaces 31c facing each other with the draw-in opening 42a therebetween. Specifically, in this embodiment, a channel that serves as a side path for the blood is formed between the draw-in opening 42a and the side surface 31c of the chamber 31, and the blood also enters from the side of the draw-in opening 42a through the side path, which is effective for blood to widely spread in the chamber 31 and more effective for forming a liquid-tight state.

The draw-in opening 42a is provided closer to the internal space R side than the end surface 31d (outlet deepest portion) most distant from the internal space R in the chamber 31. Specifically, since a space is also formed on a deep side of the draw-in opening 42a, the blood passes beside the draw-in opening 42a, goes around to the deep side, and enters the tapered outlet passage 33 from a broader range. Thus, the blood widely spreads in the chamber 31, which is more effective for forming a liquid-tight state.

Next, with reference to FIGS. 10(a) and 10(b) and FIGS. 11(a) and 11(b), aspects of outlet ports according to third to sixth embodiments of the present invention will be described. Here, a blood treatment filter according to each embodiment has a tapered outlet passage, and the tapered outlet passage provides a trigger for blood to push out bubbles during flowing, which facilitates formation of a liquid-tight state. This can prevent a reduction in filtration speed, and a desired filtration speed is obtained to allow efficient filtration treatment. In describing the blood treatment filter according to each embodiment below, the same or similar components as in the blood treatment filter 1A are denoted by the same reference numerals, and overlapping descriptions will be omitted.

In an outlet port 22C (see FIG. 10(a)) of the blood treatment filter 1C according to the third embodiment, in an outlet channel (blood lead-out passage) 28, a chamber (outlet anterior chamber) 31, and an outlet connection channel 51 that communicates with the chamber 31 are provided. In the outlet connection channel 51, an inverted tapered outlet passage 52 that communicates with the chamber 31, an intermediate channel 53, and a tapered outlet passage (outlet tapered portion) 54 are provided, and an outlet 27 connects to a downstream end of the tapered outlet passage 54.

The inverted tapered outlet passage 52 is symmetric with respect to the tapered outlet passage 54, and an inner diameter is large on the chamber 31 side and small on the outlet 27 side. Also, an inner diameter of the intermediate channel 53 is constant in a flow direction of blood, and formed of a cylindrical space. On the other hand, the tapered outlet passage 54 has an inner diameter increasing from the chamber 31 side on the internal space R side toward the outlet 27 side.

In an outlet port 22D (see FIG. 10(b)) of a blood treatment filter 1D according to the fourth embodiment, in an outlet channel (blood lead-out passage) 28, a chamber (outlet anterior chamber) 61, and a tapered outlet passage 62 that communicates with the chamber 61 are provided, and the tapered outlet passage 62 corresponds to an outlet connection channel. In this embodiment, a floor surface (lower surface) of the chamber 61 is raised in an angular shape, and near a top thereof, a draw-in opening 62a of the tapered outlet passage 62 is provided.

The tapered outlet passage 62 has an inner diameter increasing from the chamber 61 side on an internal space R side toward an outlet 27 side. Specifically, the tapered outlet passage 62 is shaped so that the diameter gradually increases in a flow direction of blood.

In an outlet port 22E (see FIG. 11(*a*)) of a blood treatment filter 1E according to the fifth embodiment, in an outlet channel (blood lead-out passage) 28, a chamber (outlet anterior chamber) 31, and an outlet connection channel 71 that communicates with the chamber 31 are provided. In the outlet connection channel 71, an inverted tapered outlet passage 72 that communicates with the chamber 31, and a tapered outlet passage (outlet tapered portion) 73 are provided, and an outlet 27 connects to a downstream end of the tapered outlet passage 73.

The inverted tapered outlet passage 72 is symmetric with respect to the tapered outlet passage 73, and an inner diameter is large on the chamber 31 side and small on the outlet 27 side. On the other hand, the tapered outlet passage 73 has an inner diameter increasing from the chamber 31 side on the internal space R side toward the outlet 27 side. Also, in this embodiment, an angle θ1 of a section of a connection area between the inverted tapered outlet passage 72 and the tapered outlet passage 73 is acute.

In an outlet port 22F (see FIG. 11(*b*)) of a blood treatment filter 1F according to the sixth embodiment, in an outlet channel (blood lead-out passage) 28, a chamber (outlet anterior chamber) 31, and an outlet connection channel 81 that communicates with the chamber 31 are provided. In the outlet connection channel 81, an inverted tapered outlet passage 82 that communicates with the chamber 31, and a tapered outlet passage (outlet tapered portion) 83 are provided, and an outlet 27 connects to a downstream end of the tapered outlet passage 83.

The inverted tapered outlet passage 82 is symmetric with respect to the tapered outlet passage 83, and an inner diameter is large on the chamber 31 side and small on the outlet 27 side. On the other hand, the tapered outlet passage 83 has an inner diameter increasing from the chamber 31 side on an internal space R side toward the outlet 27 side. Also, in this embodiment, an angle θ2 of a section of a connection area between the inverted tapered outlet passage 82 and the tapered outlet passage 83 is obtuse.

In the descriptions on the blood treatment filters according to the second to sixth embodiments, a description on the inlet port is omitted. However, in each embodiment, the inlet port and the outlet port may be of substantially the same shape to be plane-symmetric with respect to the filter material, or may be of different shapes.

EXAMPLES

Now, the present invention will be described in more detail with examples, but the present invention is not limited by the examples below.

Example 1

Using a blood treatment filter comprising an inlet side container, an outlet side container, and a leukocyte removal filter material, an inlet port thereof was connected to a storage bag via an inlet side circuit of 50 cm in length. Also, an outlet port of the filter was connected to a collection bag via an outlet side circuit of 100 cm in length. As an inlet side circuit and an outlet side circuit, tubes (conduits) made of soft vinyl chloride with an inner diameter of 3 mm and an outer diameter of 5 mm were used.

In fabrication of the blood treatment filter, the inlet side container and the outlet side container were sealed along a peripheral edge of the filter material while sandwiching the filter material to form a rectangular seal portion (first seal portion). With a longitudinal dimension of an inside of the first seal portion being 74 mm and a lateral dimension being 57 mm, an effective filtration portion was formed to be rectangular, corner portions were curved, and an effective filtration area was set to $42 \times 10^{-4}$ ($m^2$). A filter material was used in which, from an inlet toward an outlet in filtration of blood, four polyester nonwoven fabrics of air permeability of 237.3 ($cc/cm^2/sec$) and a thickness of 0.2 mm, one polyester nonwoven fabric of air permeability of 8.4 ($cc/cm^2/sec$) and a thickness of 0.4 mm, 32 polyester nonwoven fabrics of air permeability of 7.7 ($cc/cm^2/sec$) and a thickness of 0.20 mm, one polyester nonwoven fabric of air permeability of 8.4 ($cc/cm^2/sec$) and a thickness of 0.4 mm, and four polyester nonwoven fabrics of air permeability of 237.3 ($cc/cm^2/sec$) and a thickness of 0.2 mm were stacked in order. The air permeability was measured by a method based on Japanese Industrial Standards JIS L-1096, 6.27.1A.

The inlet port was sealed to the inlet side container, and the outlet port was sealed to the outlet side container. Also, as described above, after formation of the first seal portion, the inlet side container and the outlet side container were sealed outside the filter material to form a second seal portion. At this time, sealing and assembly were performed so that an inlet opening portion through which blood flows from the inlet port into the inlet side container was placed inside an uppermost portion of the first seal portion, that is, in a position 2.4 cm lower than an upper end of the effective filtration portion. Simultaneously, assembly was performed so that an outlet opening portion through which blood flows out from inside the outlet side container to the outlet port was placed inside a lowermost portion of the first seal portion, that is, in a position 2.4 cm higher than a lower end of the effective filtration portion.

Example 1 corresponds to the second embodiment described above (see FIG. 9), and an outlet port was used in which an outlet channel (blood lead-out passage) and an outlet in which a conduit of an outlet side circuit was fitted were formed. The outlet channel has a chamber that communicates with an internal space, and an outlet connection channel of 2.9 mm in length that communicates with the chamber. An upper portion of 1.4 mm of the outlet connection channel is an intermediate channel with a diameter decreased to 2 mm, and a lower portion of 1.5 mm of the outlet connection channel is a tapered outlet passage (outlet tapered portion). The tapered outlet passage is tapered to have an increasing diameter so that a diameter (inner diameter) of an upper end is 2 mm and a diameter (inner diameter) of a lower end is 3 mm. The inlet port of the same shape as the outlet port was used.

A total difference that is a sum of an upstream side difference, a difference between an inlet and an outlet of the blood treatment filter, and a downstream side difference was fixed at 150 cm. Then, as an alternative to packed erythrocytes containing a SAG-M liquid of 100 mL after removal of buffy coat derived from human whole blood of 570 mL containing a CPD-A liquid of 70 mL mainly used in Europe, similarly prepared packed erythrocytes of 300 mL derived from pig blood was injected into a storage bag, and caused to flow at room temperature using gravity. To facilitate visual check of discharge of the liquid in the storage bag, air of 20 mL was simultaneously added to the storage bag. A collection bag was previously placed on a pan scale so that a change in weight can be checked.

At this time, a time required from when the liquid to be treated started to flow to when all the liquid to be treated in the storage bag was discharged and an increase in weight of the collection bag stopped, that is, a time required for filtering all liquid was measured to be a total treatment time (minute). In the total treatment time, a time required from when the all liquid to be treated in the storage bag was discharged to when the increase in weight stopped was a collection time (minute). This test was repeated 10 times, an incidence of an air remaining phenomenon in a lower portion of the filter was checked, and also an average total treatment time and an average collection time were obtained.

For adjusting packed erythrocytes derived from pig blood, to be able to check a difference in port shape, buffy coat was removed as much as possible, and adjustment was made so that a hematocrit value was stably high, within a range of a condition actually performed in the blood center. An average hematocrit value of all prepared packed erythrocytes derived from pig blood was 63.4(%), and the packed erythrocytes were randomly used without a bias also for Example 2 and Comparative example 2 described later.

Example 2

Example 2 corresponds to the first embodiment described above (see FIG. 1 to FIG. 5), and a blood treatment filter was assembled to perform filtration in the same manner as in Example 1 except that used ports were as described below. As an outlet port according to Example 2, an outlet port was used in which an outlet channel (blood lead-out passage) and an outlet in which a conduit of an outlet side circuit was fitted were formed. The outlet channel has a chamber that communicates with an internal space, and an outlet connection channel of 2.9 mm in length that communicates with the chamber. The outlet connection channel is a tapered outlet passage (outlet tapered portion) tapered to have an increasing diameter from an upper end toward a lower end, an inner diameter (diameter) of the upper end that communicates with the chamber being decreased to 2 mm, and an inner diameter (diameter) of the lower end of the outlet connection channel being 3 mm. An inlet port of the same shape as the outlet port was used.

Comparative Example 1

Comparative example 1 corresponds to a reference form described above (see FIG. 8), a filter was assembled to perform filtration in the same manner as in Example 1 except that used ports were as described below. An outlet port was used in which an outlet channel and an outlet in which a conduit of an outlet side circuit was fitted were formed. The outlet channel has a chamber that communicates with an internal space, and a connection channel of 2.9 mm in length that communicates with the chamber. The communication channel was used that is not tapered but is cylindrical with both upper and lower ends having a diameter of 3 mm. An inlet port of the same shape as the outlet port was used.

Results of Example 1, Example 2, and Comparative Example 1 are collectively shown in Table 1.

TABLE 1

| | | EXAMPLE 1 | EXAMPLE 2 | COMPARATIVE EXAMPLE 1 |
|---|---|---|---|---|
| PORT SHAPE | INLET PORT | SAME AS OUTLET PORT | SAME AS OUTLET PORT | SAME AS OUTLET PORT |
| | OUTLET PORT | CORRESPOND TO SECOND EMBODIMENT | CORRESPOND TO FIRST EMBODIMENT | CORRESPOND TO REFERENCE FORM |
| INCIDENCE OF AIR REMAINING IN LOWER PORTION OF FILTER | | 1/10 | 0/10 | 4/10 |
| AVERAGE TOTAL TREATMENT TIME (MINUTE) | | 24.2 | 22.4 | 28.7 |
| AVERAGE COLLECTION TIME (MINUTE) | | 6.0 | 4.4 | 10.7 |

For the outlet port in Example 1, the intermediate channel is a small diameter portion with an inner diameter of 2 mm, the small diameter portion exists over a length of 1.4 mm, and the tapered outlet passage is formed therebelow. The inner diameter of the tapered outlet passage is larger on the outlet side than on the chamber side, and it is considered that providing the tapered outlet passage provides a trigger for blood to push out bubbles during flowing. Further, in Example 1, the inner diameter of the small diameter portion that communicates with the chamber is 2 mm and small, and it is considered that such thinness prevents blood from flowing along a part of a wall surface, and allows the blood to flow over the entire wall surface to act to push out air in the circuit.

For the outlet port in Example 2, the upper end of the tapered outlet passage directly connects to the chamber, and further in the inlet (starting point portion) through which blood enters the tapered outlet passage vertically downward, an angle of a portion in which the blood flows is a large angle exceeding 270 degrees. Further, the diameter (inner diameter) of the upper end of the tapered outlet passage is decreased to 2 mm. Thus, the outlet channel of the outlet port is shaped so that when the blood flowing into the outlet port reaches the inlet of the tapered outlet passage, the blood is prone to flow sideward around the inlet rather than flow downward. Thus, the blood in the chamber flows along the wall surface to prevent generation of a downward flow toward the tapered outlet passage, and the blood over the entire periphery acts to push out air in the circuit downward. Also, the outlet port in Example 2 has a feature that liquid passing resistance itself is lower because a thin portion of 2 mm is shorter than in Example 1.

For the outlet port in Comparative Example 1, the inner diameter of the inlet of the communication channel is 3 mm and large, and an angle of a portion from the chamber of the communication channel toward the communication channel is 270 degrees (an angle of a section of the starting point portion is 90 degrees). Thus, when the blood reaches the inlet of the communication channel, the blood is prone to flow along only a part of a liquid surface while leaving air in the circuit. Then, if air remains in the outlet side circuit, a height of the air does not act as a force by using the effect of gravity from height differential, and thus filtration takes time as in flowing substantially by a small difference. In particular, it is confirmed that when blood on the inlet side runs out at around the end of filtration and blood remaining in a system is collected, the air remains in the lower portion of the filter significantly increases a collection time.

Example 3

Fabrication of a blood treatment filter, and assembly of a storage bag, the filter, and a collection bag were performed in the same manner as in Example 2.

After a SAG-M liquid of 100 mL was injected into a collection bag, the collection bag was placed on an upper side, and a total difference was fixed at 150 cm. At this time, the storage bag was previously placed on a pan scale so that a change in weight can be checked.

At this time, a time required from when a SAG-M liquid starts to flow to when an increase in weight in the storage bag stops was a priming time (minute). This test was repeated ten times, an incidence of an air remaining phenomenon in a lower portion of the blood treatment filter was checked, and also an average priming time was calculated.

Comparative Example 2

The filter was assembled to perform filtration in the same manner as in Example 3 except that used ports were as described below. An outlet port in filtering blood, that is, an inlet port in priming with the SAG-M liquid of the same shape as in Example 3 was used. An inlet port in filtering blood, that is, an outlet port in priming with the SAG-M liquid had a communication channel of 2.9 mm in length in an upper portion of a circuit connection portion, and the communication channel was cylindrical with both upper and lower ends having a diameter of 3 mm.

Next, results of Example 3 and Comparative Example 2 are shown in Table 2.

TABLE 2

| PORT SHAPE | | EXAMPLE 3 | COMPARATIVE EXAMPLE 2 |
| --- | --- | --- | --- |
| PORT SHAPE | INLET PORT | SAME AS INLET PORT IN EMBODIMENT 2 | SAME AS INLET PORT IN EMBODIMENT 2 |
| | OUTLET PORT | SAME AS OUTLET PORT IN EMBODIMENT 2 | CORRESPOND TO REFERENCE FORM |
| INCIDENCE OF AIR REMAINING IN LOWER PORTION OF FILTER | | 0/10 | 2/10 |
| AVERAGE SAG-M PRIMING TIME (SECOND) | | 54.2 | 65.7 |

In Europe, so-called retro-priming is performed of priming a filter with a SAG-M liquid in a collection bag and causing the SAG-M liquid to flow toward blood. At this time, using the port in the present invention as an inlet port in filtering blood, that is, an outlet port in priming with the SAG-M liquid allows pushing-out of air in a system and efficient priming.

REFERENCE SIGNS LIST 1A, 1B, 1C, 1D, 1E, 1F . . . blood treatment filter
3 . . . filter container
5 . . . filter material
21A . . . inlet port
22A, 22B, 22C, 22D, 22E, 22F . . . outlet port
25 . . . inlet
26 . . . inlet channel (blood introduction passage)
27 . . . outlet
28 . . . outlet channel (blood lead-out passage)
30 . . . chamber (inlet posterior chamber)
31, 61 . . . chamber (outlet anterior chamber)
31a . . . floor surface (lower surface)
31c . . . side surface
31d . . . end surface (outlet deepest portion)
32 . . . tapered inlet passage (inlet tapered portion, inlet connection channel)
32a . . . communication opening
33 . . . tapered outlet passage (outlet tapered portion, outlet connection channel)
33a . . . draw-in opening
41, 51, 71, 81 . . . outlet connection channel
42a . . . draw-in opening
43, 54, 62, 73, 83 . . . tapered outlet passage (outlet tapered portion)
101 . . . storage bag
102 . . . inlet side circuit
103 . . . collection bag
104 . . . outlet side circuit
C1 . . . central axis in channel direction of tapered outlet passage
C2 . . . central axis in channel direction of tapered inlet passage
d1 . . . inner diameter of draw-in opening
d2 . . . inner diameter of communication opening
D1, D2 . . . separation distance between side surfaces
R . . . internal space
R1 . . . inlet side space
R2 . . . outlet side space
α . . . angle of section of starting point portion of tapered outlet passage
β . . . angle of section of end point portion of tapered inlet passage

The invention claimed is:

1. A blood treatment filter that treats blood introduced from an inlet and discharges the blood from an outlet, the blood treatment filter comprising:
   a filter container that introduces the blood from the inlet into an internal space, and discharges the treated blood from the outlet;
   a filter material that is housed in the filter container to partition the internal space into an inlet side space and an outlet side space, and filters the passing blood to remove a specific component;
   an inlet port that forms a blood introduction passage through which the blood flowing from the inlet to the internal space passes; and
   an outlet port that forms a blood lead-out passage through which the blood flowing from the internal space to the outlet passes;
   wherein the outlet port has an outlet anterior chamber communicating with the internal space, an outlet connection channel communicating with the outlet and having an outlet tapered portion with first and second ends, and a draw-in opening communicating between the outlet anterior chamber and the outlet connection channel,
   the outlet anterior chamber has a floor surface completely surrounding an outer periphery of the draw-in opening,
   wherein the floor surface is oriented in a plane that is perpendicular to a longitudinal plane in which the filter material is oriented, the outlet anterior chamber further comprising: a pair of side surfaces facing each other, a dome-shaped surface provided opposite the floor surface, and an end surface spaced apart from the draw-in opening, wherein the dome-shaped surface and the end surface intersect each other in a continuous arc, the draw-in opening is located at the first end of the outlet tapered portion, the outlet tapered portion having an inner surface with an inner diameter that widens from the first end towards the second end of the outlet tapered portion, wherein an acute-angled cross section is formed by an intersection of the floor surface of the outlet anterior chamber and the inner surface of the outlet tapered portion when viewed with respect to all cross-sections taken along an imaginary surface including a central axis in a channel direction of the outlet tapered portion, and wherein the floor surface and the inner surface of the outlet tapered portion, which intersect to form the acute-angled cross section, are configured to enable blood entering the outlet port to form a liquid-tight state within the outlet tapered portion.

2. The blood treatment filter according to claim 1, wherein the blood introduction passage has an inlet posterior chamber that communicates with the internal space, an inlet connection channel that communicates with the inlet and having an inlet tapered portion, and a communication opening that provides communication between the inlet posterior chamber and the inlet connection channel, the communication opening is an end point portion of the inlet tapered portion, and an inner diameter of the inlet tapered portion narrows with distance in a direction towards the communication opening.

3. The blood treatment filter according to claim 2, wherein a section of an end point portion on an internal space side of the inlet tapered portion has an acute-angled cross section when the inlet port is cut along an imaginary surface including a central axis in a channel direction of the inlet tapered portion.

4. The blood treatment filter according to claim 2, wherein the inlet posterior chamber has a ceiling surface, and the communication opening is provided in a part of the ceiling surface of the inlet posterior chamber.

5. The blood treatment filter according to claim 4, wherein the inlet posterior chamber further comprises a pair of side surfaces facing each other with the communication opening therebetween, and an inner diameter of the communication opening is smaller than a separation distance between the pair of side surfaces.

6. The blood treatment filter according to claim 5, wherein the communication opening is provided closer to the internal space side than an inlet deepest portion most distant from the internal space in the inlet posterior chamber.

7. A blood circuit comprising:
the blood treatment filter according to claim 1;
a storage bag that stores blood;
a collection bag that stores blood after treatment with the blood treatment filter;
an inlet side circuit portion that connects the storage bag and the inlet port of the blood treatment filter; and
an outlet side circuit portion that connects the outlet port of the blood treatment filter and the collection bag.

8. A blood treatment method that uses the blood treatment filter according to claim 1 and filters blood by gravity.

* * * * *